(12) United States Patent
Sprinkle et al.

(10) Patent No.: US 7,621,274 B2
(45) Date of Patent: Nov. 24, 2009

(54) NASAL MASK

(75) Inventors: Thomas B. Sprinkle, Rocky River, OH (US); Mary B Whitesel, Grafton, OH (US); Mark E. Rosenkranz, Panna, OH (US); Neal Joseph Curran, Lakewood, OH (US); Valentine A. Hodos, Cleveland, OH (US)

(73) Assignee: Invacare Corporation, Elyria, OH (US)

( * ) Notice: Subject to any disclaimer, the term of this patent is extended or adjusted under 35 U.S.C. 154(b) by 1124 days.

(21) Appl. No.: 10/601,729

(22) Filed: Jun. 23, 2003

(65) Prior Publication Data

US 2004/0182398 A1 Sep. 23, 2004

Related U.S. Application Data

(63) Continuation-in-part of application No. 10/394,731, filed on Mar. 22, 2003, now Pat. No. 7,290,546.

(51) Int. Cl.
*A62B 18/02* (2006.01)
*A62B 18/08* (2006.01)

(52) U.S. Cl. .................. 128/206.21; 128/206.24; 128/206.28; 128/207.11; 128/207.13

(58) Field of Classification Search ............ 128/205.25, 128/206.12, 206.21, 206.24, 206.26, 206.27, 128/206.28, 207.13, 207.18, 200.25
See application file for complete search history.

(56) References Cited

U.S. PATENT DOCUMENTS

| 781,516 | A | 1/1905 | Guthrie, Jr. |
| 812,706 | A | 2/1906 | Warbasse |
| 844,097 | A | 2/1907 | Caldwell |
| 1,048,491 | A | 12/1912 | Butcher |
| 1,081,745 | A | 12/1913 | Johnston et al. |
| 1,192,186 | A | 7/1916 | Greene |
| 1,206,045 | A | 11/1916 | Smith |
| 1,632,449 | A | 4/1927 | McKesson |
| 1,635,275 | A | 7/1927 | Johnson |
| 1,653,572 | A | 12/1927 | Jackson |
| 1,926,027 | A | 9/1933 | Biggs |
| 2,123,353 | A | 7/1938 | Catt |
| 2,133,699 | A * | 10/1938 | Heidbrink .............. 128/206.24 |
| 2,241,535 | A | 5/1941 | Boothby et al. |
| 2,248,477 | A | 7/1941 | Lombard |
| 2,254,854 | A | 9/1941 | O'Connell |

(Continued)

FOREIGN PATENT DOCUMENTS

AU  A-32914/95  2/1996

(Continued)

OTHER PUBLICATIONS

Communication pursuant to Article 96(2) EPC for European application No. 03 745 562.3-2310.

(Continued)

*Primary Examiner*—Justine R Yu
*Assistant Examiner*—Clinton Ostrup
(74) *Attorney, Agent, or Firm*—Calfee, Halter & Griswold LLP

(57) ABSTRACT

A nasal mask of the type for delivering gas for example to ease or assist the breathing process includes a shell and a cushion connected with the shell. The shell has a side wall and a retaining ring disposed inside the side wall. The side wall and the retaining ring define a gap extending around the shell. The cushion has a side wall with an outer peripheral edge portion including a tongue extending around the cushion. The tongue of the cushion is received in the gap in the shell to secure the cushion to the shell. Various straps assemblies and forehead adjusters for nasal masks are also shown.

13 Claims, 8 Drawing Sheets

U.S. PATENT DOCUMENTS

| | | | |
|---|---|---|---|
| 2,317,608 A | 4/1943 | Heidbrink | |
| 2,371,965 A | 3/1945 | Lehmberg | |
| 2,376,871 A | 5/1945 | Fink | |
| 2,415,846 A | 2/1947 | Randall | |
| 2,438,058 A | 3/1948 | Kincheloe | |
| 2,578,621 A | 12/1951 | Yant | |
| 2,765,788 A | 10/1956 | Raiche | |
| 2,939,458 A | 6/1960 | Lundquist | |
| 3,013,556 A | 12/1961 | Galleher, Jr. | |
| 3,182,659 A | 5/1965 | Blout | |
| 3,189,027 A | 6/1965 | Barlett, Jr. | |
| 3,193,624 A | 7/1965 | Webb et al. | |
| 3,238,943 A | 3/1966 | Holley | |
| 3,315,674 A | 4/1967 | Bloom et al. | |
| 3,330,273 A | 7/1967 | Bennett | |
| 3,330,274 A | 7/1967 | Bennett | |
| 3,362,420 A | 1/1968 | Blackburn et al. | |
| 3,363,833 A | 1/1968 | Laerdal | |
| 3,556,122 A | 1/1971 | Laerdal | |
| 3,580,051 A | 5/1971 | Blevins | 73/40 |
| 3,700,000 A | 10/1972 | Hesse et al. | 137/494 |
| 3,720,235 A | 3/1973 | Schrock | 138/137 |
| 3,725,953 A | 4/1973 | Johnson et al. | 2/14 W |
| 3,779,164 A | 12/1973 | Study | 101/334 |
| 3,982,532 A | 9/1976 | Halldin et al. | 128/146 |
| 4,077,404 A | 3/1978 | Elam | 128/145.8 |
| 4,167,185 A | 9/1979 | Lewis | 128/146.7 |
| 4,226,234 A | 10/1980 | Gunderson | 128/205.24 |
| 4,245,632 A | 1/1981 | Houston | 128/205.13 |
| 4,263,908 A | 4/1981 | Mizerak | 128/205.25 |
| 4,266,540 A | 5/1981 | Panzik et al. | 128/207.13 |
| 4,304,229 A | 12/1981 | Curtin | 128/201.11 |
| 4,328,797 A | 5/1982 | Rollins, III et al. | 128/202.27 |
| 4,347,205 A | 8/1982 | Stewart | 264/130 |
| 4,354,488 A | 10/1982 | Bartos | 128/205.25 |
| 4,402,316 A | 9/1983 | Gadberry | 128/201.15 |
| 4,412,537 A | 11/1983 | Tiger | 128/204.17 |
| 4,467,799 A | 8/1984 | Steinberg | 128/206.14 |
| 4,522,639 A | 6/1985 | Ansite et al. | 55/314 |
| 4,558,710 A | 12/1985 | Eichler | 128/720 |
| 4,559,940 A | 12/1985 | McGinnis | 128/206.26 |
| 4,616,647 A | 10/1986 | McCreadie | 128/206.19 |
| 4,622,964 A | 11/1986 | Flynn | 128/205.24 |
| 4,655,213 A | 4/1987 | Rapoport et al. | 128/205.25 |
| 4,665,570 A | 5/1987 | Davis | 2/428 |
| 4,671,271 A | 6/1987 | Bishop et al. | 128/206.11 |
| 4,677,975 A | 7/1987 | Edgar et al. | 128/200.14 |
| 4,677,977 A | 7/1987 | Wilcox | 128/206.24 |
| H397 H | 1/1988 | Stark | 128/206.24 |
| 4,739,755 A | 4/1988 | White et al. | 128/207.12 |
| 4,770,169 A | 9/1988 | Schmoegner et al. | 128/207.13 |
| 4,774,941 A | 10/1988 | Cook | 128/205.13 |
| 4,782,832 A | 11/1988 | Trimble et al. | 128/207.18 |
| 4,799,477 A | 1/1989 | Lewis | 128/206.24 |
| 4,809,692 A | 3/1989 | Nowacki et al. | 128/206.24 |
| 4,819,629 A | 4/1989 | Jonson | 128/203.22 |
| 4,821,713 A | 4/1989 | Bauman | 128/205.13 |
| 4,841,953 A | 6/1989 | Dodrill | 128/202.27 |
| 4,848,334 A | 7/1989 | Bellm | 128/207.11 |
| 4,848,366 A | 7/1989 | Aita et al. | 128/863 |
| 4,907,584 A | 3/1990 | McGinnis | 128/206.24 |
| 4,910,806 A | 3/1990 | Baker et al. | 2/452 |
| 4,919,128 A | 4/1990 | Kopala et al. | 128/207.18 |
| 4,938,210 A | 7/1990 | Shene | 128/203.12 |
| 4,938,212 A | 7/1990 | Snook et al. | 128/205.24 |
| 4,944,310 A | 7/1990 | Sullivan | 128/848 |
| 4,971,051 A | 11/1990 | Toffolon | 128/206.26 |
| 4,986,269 A | 1/1991 | Hakkinen | 128/204.23 |
| 4,989,596 A | 2/1991 | Macris et al. | 128/201.28 |
| 4,989,599 A | 2/1991 | Carter | 128/207.18 |
| 5,005,568 A | 4/1991 | Loescher et al. | 128/202.28 |
| 5,005,571 A | 4/1991 | Dietz | 128/205.25 |
| 5,038,776 A | 8/1991 | Harrison et al. | 128/207.11 |
| 5,042,473 A | 8/1991 | Lewis | 128/205.24 |
| 5,046,200 A | 9/1991 | Feder | 2/452 |
| 5,063,922 A | 11/1991 | Hakkinen | 128/200.16 |
| 5,069,205 A | 12/1991 | Urso | 128/201.24 |
| 5,109,839 A | 5/1992 | Blasdell et al. | 128/203.12 |
| 5,109,840 A | 5/1992 | Daleiden | 128/205.13 |
| 5,117,819 A | 6/1992 | Servidio et al. | 128/204.18 |
| 5,121,745 A | 6/1992 | Israel | 128/202.28 |
| 5,133,347 A | 7/1992 | Huennebeck | 128/205.24 |
| 5,140,980 A | 8/1992 | Haughey et al. | 128/201.25 |
| 5,140,982 A | 8/1992 | Bauman | 128/205.13 |
| 5,159,938 A | 11/1992 | Laughlin | 128/858 |
| 5,178,138 A | 1/1993 | Walstrom et al. | 128/200.23 |
| D333,015 S | 2/1993 | Farmer et al. | D29/8 |
| 5,227,173 A * | 7/1993 | Sherwood | 425/143 |
| 5,231,983 A | 8/1993 | Matson et al. | 128/207.14 |
| 5,233,978 A | 8/1993 | Callaway | 128/205.25 |
| 5,265,595 A | 11/1993 | Rudolph | 128/204.18 |
| 5,279,289 A | 1/1994 | Kirk | 128/205.23 |
| 5,280,784 A | 1/1994 | Kohler | 128/200.14 |
| 5,311,862 A | 5/1994 | Blasdell et al. | 128/205.25 |
| 5,322,057 A | 6/1994 | Raabe et al. | 128/203.12 |
| 5,343,878 A | 9/1994 | Scarberry et al. | 128/898 |
| 5,357,951 A | 10/1994 | Ratner | 128/205.24 |
| 5,372,130 A | 12/1994 | Stern et al. | 128/205.25 |
| 5,388,571 A | 2/1995 | Roberts et al. | 128/203.12 |
| 5,404,871 A | 4/1995 | Goodman et al. | 128/200.14 |
| 5,419,318 A | 5/1995 | Tayebi | 128/205.27 |
| 5,429,126 A | 7/1995 | Bracken | 128/207.11 |
| 5,429,683 A | 7/1995 | Le Mitoard | 128/206.24 |
| 5,431,158 A | 7/1995 | Tirotta | 128/206.21 |
| 5,438,981 A | 8/1995 | Starr et al. | 128/205.24 |
| 5,441,046 A | 8/1995 | Starr et al. | 128/207.11 |
| 5,477,852 A | 12/1995 | Landis et al. | 128/207.18 |
| 5,479,920 A | 1/1996 | Piper et al. | 128/204.23 |
| 5,488,948 A | 2/1996 | Dubruille et al. | 128/207.11 |
| 5,492,116 A | 2/1996 | Scarberry et al. | 128/206.24 |
| 5,501,214 A | 3/1996 | Sabo | 128/205.24 |
| 5,509,404 A | 4/1996 | Lloyd et al. | 128/200.14 |
| 5,517,986 A | 5/1996 | Starr et al. | 128/206.24 |
| 5,538,000 A | 7/1996 | Rudolph | 128/205.25 |
| 5,540,223 A | 7/1996 | Starr et al. | 128/205.25 |
| 5,546,936 A | 8/1996 | Virag et al. | 128/207.14 |
| 5,558,090 A | 9/1996 | James | 128/207.18 |
| RE35,339 E | 10/1996 | Rapoport | 128/204.18 |
| 5,560,354 A | 10/1996 | Berthon-Jones et al. | 128/205.25 |
| 5,570,682 A | 11/1996 | Johnson | 128/200.14 |
| 5,570,689 A | 11/1996 | Starr et al. | 128/207.11 |
| D377,089 S | 12/1996 | Starr et al. | D24/110.1 |
| 5,592,938 A | 1/1997 | Scarberry et al. | 128/206.24 |
| 5,608,647 A | 3/1997 | Rubsamen et al. | 364/509 |
| 5,642,730 A | 7/1997 | Baran | 128/207.14 |
| 5,647,355 A | 7/1997 | Starr et al. | 128/205.24 |
| 5,647,357 A | 7/1997 | Barnett et al. | 128/206.24 |
| 5,649,532 A | 7/1997 | Griffiths | 128/206.24 |
| 5,649,533 A | 7/1997 | Oren | 128/207.12 |
| 5,655,520 A | 8/1997 | Howe et al. | 128/203.13 |
| 5,655,527 A | 8/1997 | Scarberry et al. | 128/206.24 |
| 5,657,752 A | 8/1997 | Landis et al. | 128/207.13 |
| 5,662,101 A | 9/1997 | Ogden et al. | 128/205.25 |
| 5,666,946 A | 9/1997 | Langenback | 128/200.16 |
| 5,673,690 A | 10/1997 | Tayebi et al. | 128/206.24 |
| D385,960 S | 11/1997 | Rudolph | D24/110.4 |
| 5,685,296 A | 11/1997 | Zdrojkowski et al. | 128/205.24 |
| 5,690,102 A | 11/1997 | Bertheau et al. | 128/207.11 |
| D388,873 S | 1/1998 | Richards et al. | D24/110.4 |
| 5,715,814 A | 2/1998 | Ebers | 128/206.18 |
| 5,724,965 A | 3/1998 | Handke et al. | 128/207.13 |
| 5,738,094 A | 4/1998 | Hoftman | 128/206.26 |
| 5,746,201 A | 5/1998 | Kidd | 128/206.24 |

| | | | | | | |
|---|---|---|---|---|---|---|
| 5,758,642 A | 6/1998 | Choi | 128/206.21 | AU | 712236 | 11/1999 |
| 5,813,423 A | 9/1998 | Kirchgeorg | 128/202.28 | AU | 724360 | 9/2000 |
| 5,832,918 A | 11/1998 | Pantino | 128/205.25 | AU | 728849 | 1/2001 |
| D402,755 S | 12/1998 | Kwok | D24/110.4 | CA | 1039144 | 9/1978 |
| 5,884,624 A | 3/1999 | Barnett et al. | 128/206.24 | CA | 2261790 | 2/1998 |
| 5,887,587 A | 3/1999 | Groenke | 128/207.13 | CA | 2295457 | 7/2000 |
| 5,896,857 A | 4/1999 | Hely et al. | 128/205.24 | CA | 2298129 | 8/2000 |
| 5,921,239 A | 7/1999 | McCall et al. | 128/205.25 | DE | 159396 A | 3/1905 |
| D412,745 S | 8/1999 | Scheu | D24/110.4 | DE | 207751 | 4/1907 |
| 5,937,851 A | 8/1999 | Serowski et al. | 128/202.27 | DE | 459104 C1 | 4/1928 |
| 5,937,855 A | 8/1999 | Zdrojkowski et al. | 128/205.24 | DE | 701690 C1 | 1/1941 |
| 5,941,245 A | 8/1999 | Hannah et al. | 128/207.11 | DE | 1104122 | 4/1961 |
| 5,954,052 A | 9/1999 | McDonald et al. | 128/206.27 | DE | 3015279 A1 | 10/1981 |
| 5,957,132 A | 9/1999 | McDonald et al. | 128/207.11 | DE | 3345067 A1 | 5/1985 |
| 6,029,660 A | 2/2000 | Calluaud et al. | 128/203.12 | DE | 3537505 A1 | 4/1987 |
| 6,035,852 A | 3/2000 | Hoftman | 128/206.26 | DE | 3539073 A1 | 5/1987 |
| 6,039,044 A | 3/2000 | Sulivan | 128/205.25 | DE | 4004157 C1 | 4/1991 |
| D428,987 S | 8/2000 | Kwok | D24/110.4 | DE | 4343205 A1 | 6/1995 |
| D428,988 S | 8/2000 | Smart | D24/110.4 | DE | 19735359 A1 | 1/1998 |
| 6,112,746 A | 9/2000 | Kwok et al. | 128/207.13 | DE | 29723101 U1 | 5/1998 |
| 6,119,693 A | 9/2000 | Kwok et al. | 128/207.11 | DE | 3707952 A1 | 9/1998 |
| 6,119,694 A | 9/2000 | Correa et al. | 128/207.13 | DE | 29810846 U1 | 12/1999 |
| 6,123,071 A | 9/2000 | Berthon-Jones et al. | 128/204.18 | DE | 199 62 515 A 1 | 7/2001 |
| 6,123,082 A | 9/2000 | Berthon-Jones | 128/863 | EP | 0054154 | 10/1981 |
| D435,650 S | 12/2000 | Kwok | D24/110.4 | EP | 0178925 | 10/1985 |
| 6,189,532 B1 | 2/2001 | Hely et al. | 128/205.24 | EP | 0252052 | 7/1987 |
| 6,192,866 B1 | 2/2001 | Araki et al. | 123/479 | EP | 0264772 A1 | 10/1987 |
| 6,196,223 B1 | 3/2001 | Belfer et al. | 128/206.25 | EP | 0386605 A1 | 2/1990 |
| 6,341,383 B1 | 1/2002 | Beltrani | | EP | 0427474 A2 | 11/1990 |
| 6,357,440 B1 | 3/2002 | Hansen et al. | 128/206.19 | EP | 0462701 A1 | 5/1991 |
| 6,357,441 B1 | 3/2002 | Kwok et al. | 128/207.14 | EP | 0602424 B1 | 11/1993 |
| 6,374,826 B1 | 4/2002 | Gunaratnam et al. | | EP | 0608684 A1 | 1/1994 |
| 6,412,487 B1 | 7/2002 | Gunaratnam et al. | 128/206.24 | EP | 0697225 B1 | 7/1995 |
| 6,422,238 B1 | 7/2002 | Lithgow | 128/207.11 | EP | 0747078 | 6/1996 |
| 6,439,230 B1 | 8/2002 | Gunaratnam et al. | 128/206.21 | EP | 0821978 A2 | 7/1997 |
| 6,463,931 B1 | 10/2002 | Kwok et al. | 128/207.11 | EP | 958841 | 11/1999 |
| 6,467,483 B1 | 10/2002 | Kopacko et al. | | EP | 1 027 905 A2 | 8/2000 |
| 6,520,182 B1 | 2/2003 | Gunaratnam | | EP | 1 266 674 A | 12/2002 |
| 6,532,961 B1 | 3/2003 | Kwok et al. | | FR | 1 100 270 | 5/1954 |
| 6,550,070 B2 | 4/2003 | Wiegand | | FR | 2574657 A1 | 6/1986 |
| 6,679,261 B2 | 1/2004 | Lithgow et al. | | FR | 268725 A1 | 8/1991 |
| 6,691,707 B1 | 2/2004 | Gunaratnam et al. | | FR | 2749176 A1 | 12/1997 |
| 6,694,532 B2 | 2/2004 | Chen | | GB | 848215 | 9/1960 |
| 6,701,927 B2 * | 3/2004 | Kwok et al. | 128/207.13 | GB | 1395391 | 5/1975 |
| 6,823,869 B2 * | 11/2004 | Raje et al. | 128/206.24 | GB | 1467828 | 3/1977 |
| 6,832,610 B2 | 12/2004 | Gradon | | GB | 2145335 A | 3/1985 |
| 7,007,696 B2 * | 3/2006 | Palkon et al. | 128/207.13 | GB | 2164569 | 3/1986 |
| 7,207,334 B2 * | 4/2007 | Smart | 128/206.24 | GB | 2147506 A | 4/1987 |
| 2001/0035188 A1 | 11/2001 | Gleason et al. | 128/205.25 | GB | 2267648 A | 7/1996 |
| 2002/0005198 A1 | 1/2002 | Kwok et al. | 128/207.11 | JP | 9216240 A | 8/1997 |
| 2002/0005201 A1 | 1/2002 | Gradon et al. | 128/207.11 | WO | WO 80/01044 | 5/1980 |
| 2002/0014241 A1 | 2/2002 | Gradon et al. | 128/205.25 | WO | WO 82/03548 | 10/1982 |
| 2002/0023649 A1 | 2/2002 | Gunaratnam et al. | 128/205.25 | WO | WO 86/06969 | 12/1986 |
| 2002/0023650 A1 | 2/2002 | Gunaratnam et al. | 128/205.25 | WO | WO 87/01950 | 4/1987 |
| 2002/0026934 A1 | 3/2002 | Lithgow et al. | 128/97.1 | WO | WO 91/03277 | 3/1991 |
| 2002/0029780 A1 | 3/2002 | Frater et al. | 128/206.24 | WO | WO 92/15353 | 9/1992 |
| 2002/0029781 A1 | 3/2002 | Kwok et al. | 128/207.13 | WO | WO 92/20395 | 11/1992 |
| 2002/0083948 A1 | 7/2002 | Kwok et al. | 128/206.24 | WO | WO 94/02190 | 2/1994 |
| 2002/0100479 A1 * | 8/2002 | Scarberry et al. | 128/206.24 | WO | WO 94/16759 | 8/1994 |
| 2002/0104540 A1 | 8/2002 | Kwok et al. | 128/205.25 | WO | WO 94/20051 | 1/1995 |
| 2002/0108613 A1 | 8/2002 | Gunaratnam et al. | 128/205.25 | WO | WO 95/02428 | 1/1995 |
| 2002/0134388 A1 | 9/2002 | Chang | | WO | WO 96/17643 | 6/1996 |
| 2002/0148473 A1 | 10/2002 | Kwok et al. | 128/207.11 | WO | WO 96/25983 | 8/1996 |
| 2002/0157672 A1 | 10/2002 | Gunaratnam et al. | 128/205.25 | WO | WO 96/39206 | 12/1996 |
| 2002/0185134 A1 | 12/2002 | Bishop | | WO | WO 97/07847 | 3/1997 |
| 2003/0019495 A1 | 1/2003 | Palkon et al. | 128/206.21 | WO | WO 97/41911 | 11/1997 |
| 2003/0075180 A1 | 4/2003 | Raje et al. | | WO | WO 98/04310 | 2/1998 |
| | | | | WO | WO 98/11930 | 3/1998 |
| | | | | WO | WO 98/18514 | 5/1998 |

FOREIGN PATENT DOCUMENTS

| | | |
|---|---|---|
| AU | A-41018/97 | 4/1998 |
| AU | A-89312/98 | 1/1999 |
| WO | WO 98/24499 | 6/1998 |
| WO | WO 98/26829 | 6/1998 |
| WO | WO 98/26830 | 6/1998 |
| WO | WO 98/34665 | 8/1998 |

| | | |
|---|---|---|
| WO | WO 98/48878 | 11/1998 |
| WO | WO 00/57942 | 10/2000 |
| WO | WO 00/78381 | 12/2000 |
| WO | WO 00/78382 | 12/2000 |
| WO | WO 00/78383 A1 | 12/2000 |
| WO | WO 00/78384 | 12/2000 |
| WO | WO 02/45784 | 6/2002 |
| WO | WO 03/082406 A | 10/2003 |

OTHER PUBLICATIONS

PCT Search Report from PCT/US2003/008773; p. 1-9.
PCT Search Report and Written Opinion from PCT/US2004/016192; p. 1-22.
Communications from European Application No. 03745562.3-2310, mailed Jul. 12, 2007, 6 pages.

* cited by examiner

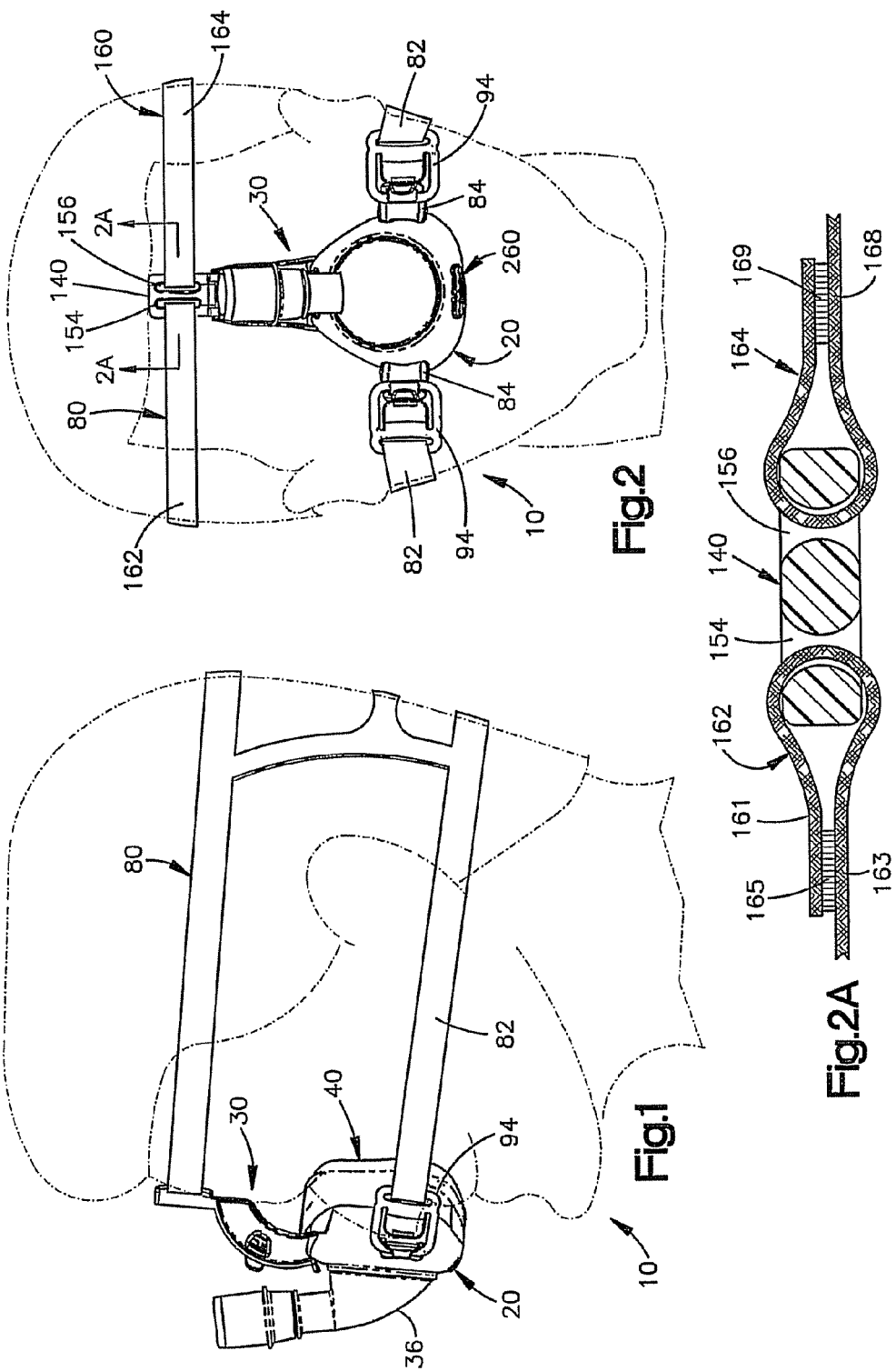

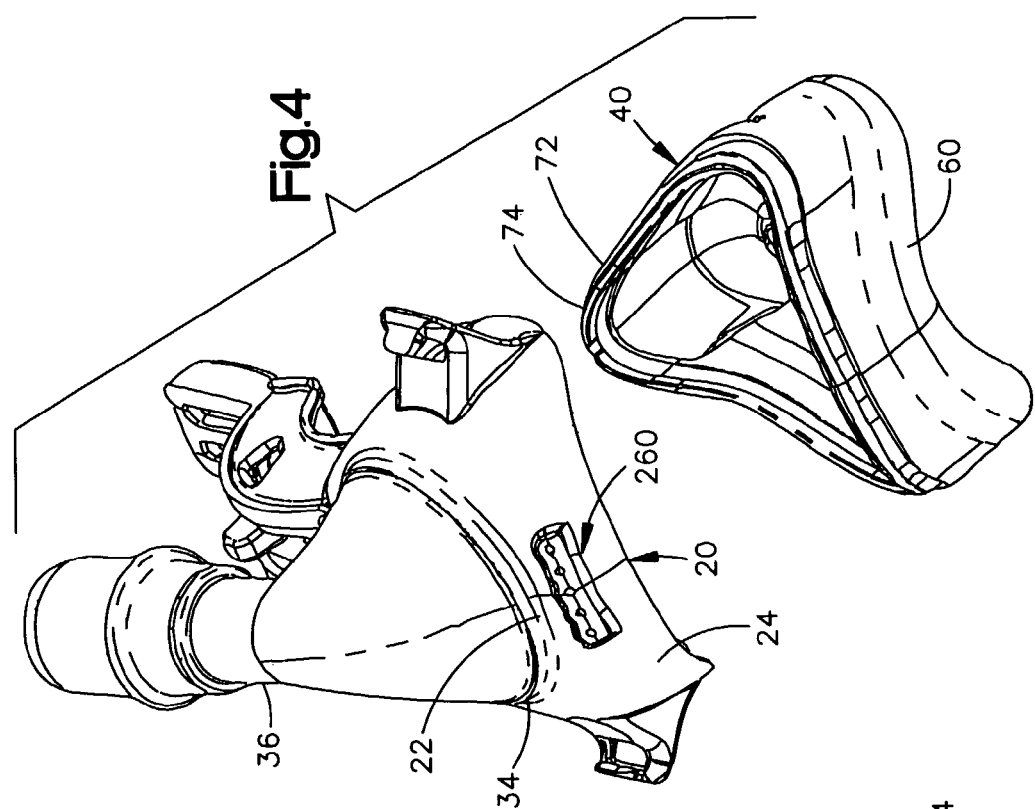
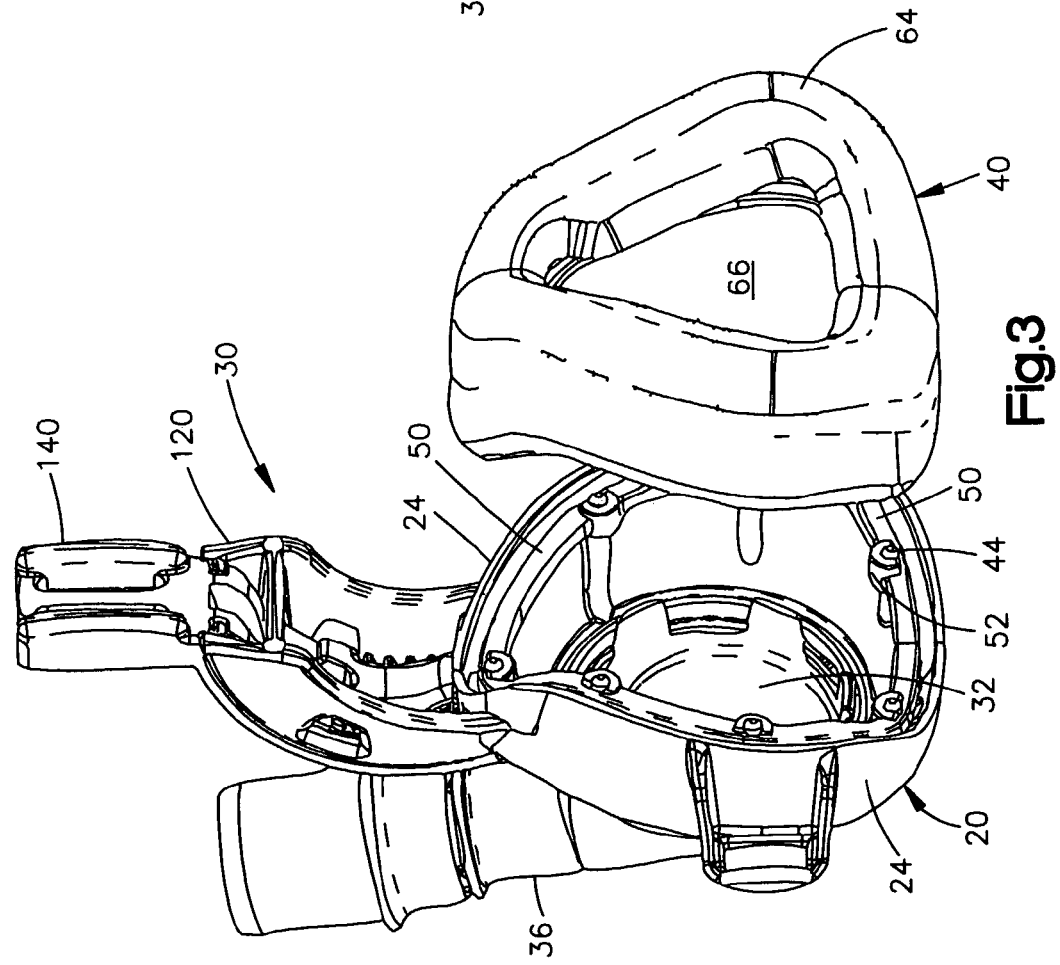

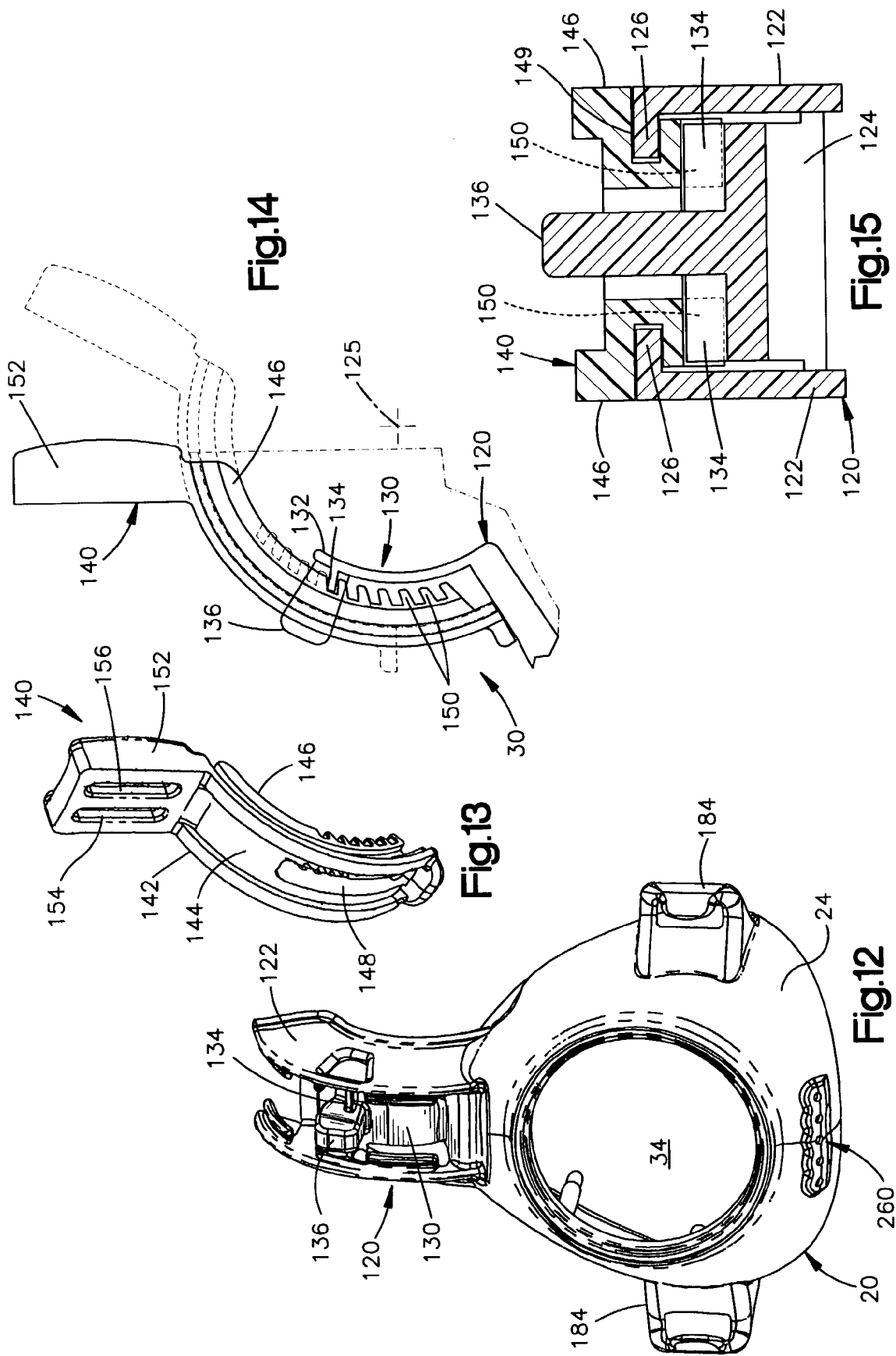

NASAL MASK

RELATED APPLICATION

This application is a continuation in part of U.S. application Ser. No. 10/394,731 filed on Mar. 22, 2003, now U.S. Pat. No. 7,290,546 entitled "Nasal Mask", having the same assignee as this application, the entire disclosure of which is fully incorporated herein by reference.

BACKGROUND OF THE INVENTION

This invention pertains to a nasal mask. Nasal masks may be used to deliver gases of controlled composition, at a controlled pressure, and at a controlled flow rate, to a person's nasal passages, for inhalation. Gas composition typically is controlled to achieve a particular medical goal, such as anesthesiology or medication or oxygenation. Gas pressure typically is controlled to ease or assist the breathing process, made difficult for example due to high altitude or a medical condition afflicting the user.

The nasal mask described here is particularly useful with continuous positive airway pressure ("CPAP") treatment for sleep disorders, such as obstructive sleep apnea. Pursuant to this treatment the user wears a nasal mask while sleeping. Gas is delivered to the nasal mask at a pressure above atmospheric pressure. This helps the user to breathe more normally during sleep. Further descriptions of CPAP treatments and devices can be found in U.S. Pat. Nos. 5,199,424 and 5,433,193, which are hereby fully incorporated by reference. The mask may be used in the home as well as in institutional settings, such as long term care facilities.

The nasal mask described here also is particularly useful in a bi-level or non-invasive ventilator. It may be used to treat chronic obstructive pulmonary disease (COPD), congested heart failure (CHF), and/or gastro esophageal reflux disorder (GERD)).

BRIEF DESCRIPTION OF THE DRAWINGS

The foregoing and other features of the present invention will become apparent to one skilled in the art to which the present invention relates upon consideration of the following description of the invention with reference to the accompanying drawings, in which:

FIG. 1 is a side elevational view of a nasal mask constructed in accordance with a first embodiment of the invention, shown in use on a user's head;

FIG. 2 is a front elevational view of the mask of FIG. 1

FIG. 2A is an enlarged schematic view of a portion of the mask of FIG. 2;

FIG. 3 is an exploded perspective view of portions of the mask of FIG. 1 including the shell and the cushion;

FIG. 4 is another exploded perspective view of portions of the mask of FIG. 1 including the shell and the cushion;

FIG. 12 is a front perspective view of the shell including a fixed part of the forehead support assembly;

FIG. 13 is a perspective view of an adjuster that forms a movable part of the forehead support assembly;

FIG. 14 is a schematic side elevational view of the portions of the forehead support assembly;

FIG. 15 is a sectional view of portions of the forehead support assembly;

DETAILED DESCRIPTION

Figure 5:
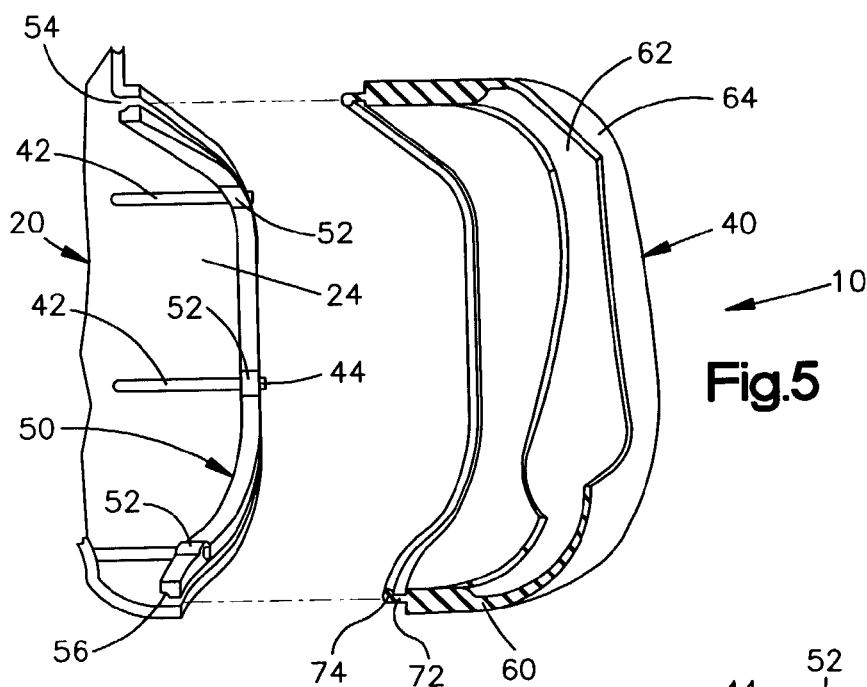
FIG. 5 is an exploded perspective schematic view showing assembly of the cushion to the shell.

The present invention relates to a nasal mask. The invention is applicable to masks of differing constructions. As representative of the invention, FIGS. 1 and 2 illustrate a nasal mask 10 constructed in accordance with a first embodiment of the invention.

The mask 10 includes a shell 20. A forehead support assembly 30 extends upward from the shell 20. A face cushion 40 is supported on the shell 20. The mask 10 also includes headgear 80 connected with the forehead support assembly 30 and with the shell 20, for helping to hold the mask on the user's head.

The shell 20 is preferably made of a rigid plastic material, which is preferably optically transparent and impermeable to gas or air. The shell 20 has a rounded triangular configuration when viewed from the front, being narrower on top by the nasal bridge region and wider by the base of the nose. The shell 20 includes a front wall 22 (FIG. 4) and a side wall 24. The forehead support assembly 30 extends upward from the side wall 24 of the shell 20.

The front wall 22 and the side wall 24 of the shell 20 define a central chamber 32 in the mask 10. A circular inlet aperture 34 in the front wall 22 of the shell 20 permits gas to enter the central chamber 32. A gas inlet tube 36 is rotatably attached to the front wall 22 of the shell 20 so that it covers the inlet aperture 32. Gas to be delivered to the patient flows into the shell 20 through the gas inlet tube 36, and into the central chamber 32 in the shell. The cushion 40 covers the wearer's nose and directs the gas from the central chamber 32 into the user's nasal passages, while blocking flow of gas out of the sides of the mask 10.

Figure 7:
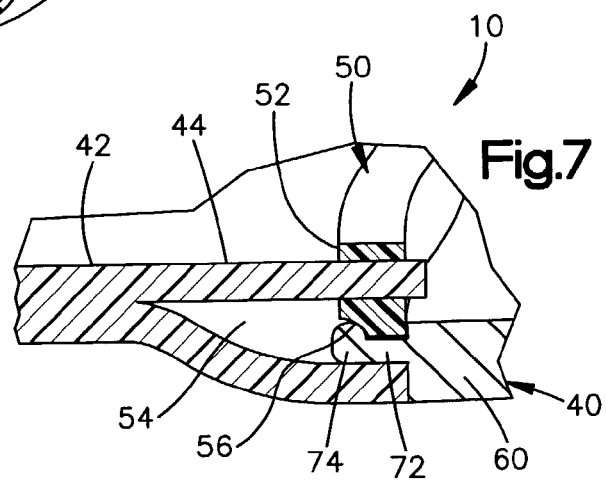
FIG. 7 is an enlarged sectional view showing portions of the cushion and shell assembled to each other.
Figure 6:
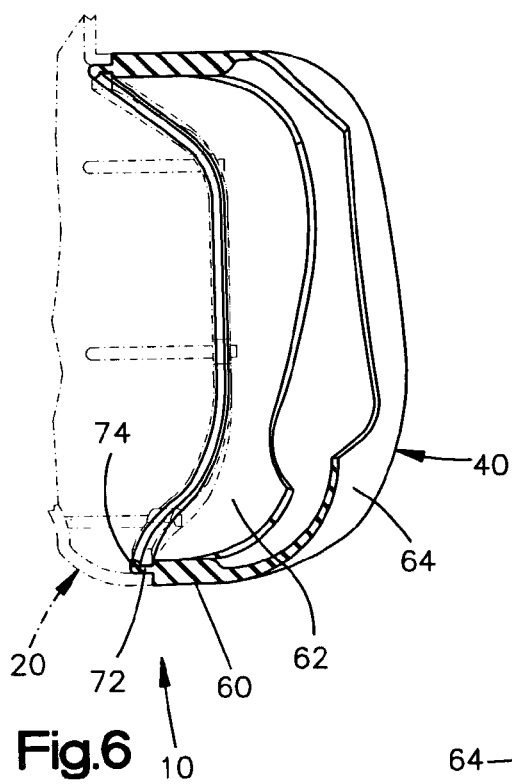
FIG. 6 is schematic view showing the cushion assembled to the shell.

The shell 20 has a plurality of molded-in ribs 42 (FIGS. 5-7) on the inner side surface of the side wall 24. The ribs 42 are spaced apart around the side wall 24. Each one of the ribs 42 has an end portion 44 that projects inwardly from the side wall 24 of the shell 20 to form a post.

The shell 20 includes a retaining ring 50 for retaining the cushion 40 on the shell. The retaining ring 50 is a one piece molded plastic member that is fixed inside the shell 20. The retaining ring 50 could be formed in another manner, or made from more than one piece.

The retaining ring 50 has a non-planar configuration that closely follows the configuration of the outer peripheral edge of the shell side wall 24. The ring 50 has a plurality of sleeves 52 spaced apart along the ring at locations that align with the posts 44 on the shell 20, when the ring is mounted on the shell.

To secure the ring 50 to the shell 20, the sleeves 52 on the ring are heat staked on the posts 44 of the shell. When the ring 50 is secured to the shell 20, a gap 54 is formed outward of the ring and inward of the side wall 24 of the shell. The gap 54 extends completely around the ring 50 and inside the side wall 24 of the shell 20. The retaining ring 50 in cross-section has a notch 56 (FIG. 7) presented away from the outer peripheral edge of the sidewall 24 of the shell 20 and toward the side wall of the shell, in a direction along the length of the ribs 42.

The cushion 40 serves two basic functions: user comfort and sealing. Thus the cushion 40 is preferably made from a bio-friendly elastomeric material which is both substantially gas impermeable and elastic enough to conform comfortably to the contours of a person's face. A preferred material is silicone. The cushion 40 may take any appropriate shape; the shape shown in the drawings is preferred. The cushion 40 is preferably molded as one piece, as shown in the illustrated embodiment.

The cushion 40 has a side wall 60, an inner wall 62, and an outer wall 64. The side wall 60 of the cushion 40 extends completely around the cushion.

The outer wall 64, which is the portion of the cushion 40 that contacts the user's face, extends laterally inward from the side wall 60. The outer wall 64 has a generally triangular central opening 66, which receives the user's nose, for enabling passage of gas from the central chamber 32 of the mask 10 into the user's nasal passages. The outer wall 64 of the cushion 40 extends completely around the cushion. Thus, when the mask 10 is used, there is complete sealing contact between the outer wall 64 of the cushion 40 and the user's face.

The inner wall 62 of the cushion 40, like the outer wall 64, extends laterally inward from the side wall 60. The inner wall 62 is thicker than the outer wall 64. As a result, the inner wall 62 is stiffer and stronger than the outer wall 64.

Figure 8:
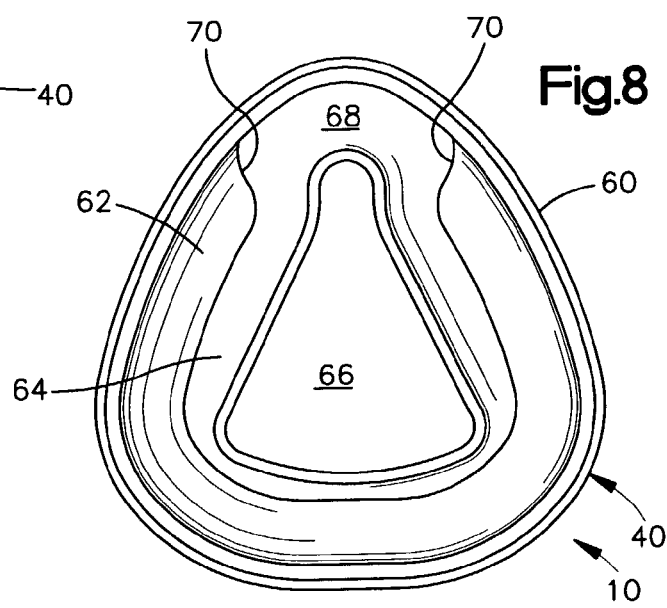
FIG. 8 is an inside elevational view of the cushion.
Figure 9:
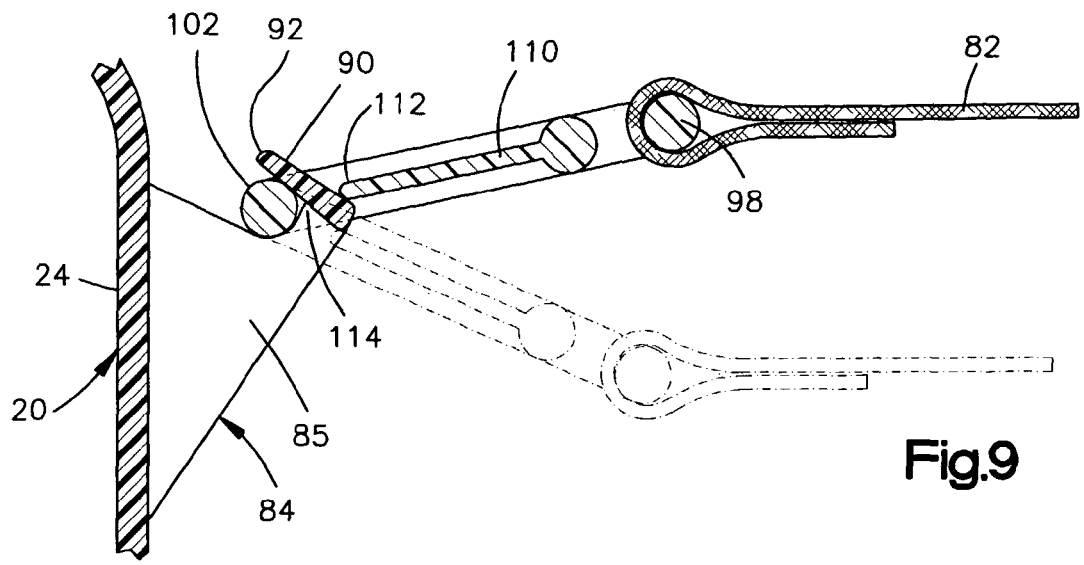
FIG. 9 is a schematic enlarged view of a side strap connector that forms part of the mask of FIG. 1.
Figure 10:
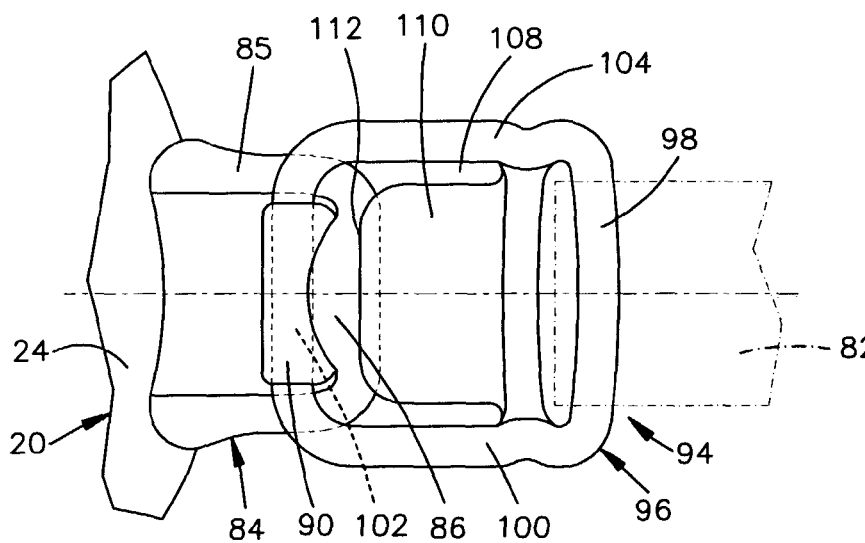
FIG. 10 is an elevational view showing the strap connector of FIG. 9 in a connected condition.

The inner wall 62 of the cushion 40 extends for most, but not all, of the extent of the outer wall 64. The inner wall 62 is discontinuous (not present) in the region of the nasal bridge. A gap 68 (FIG. 8) is formed between two ends 70 of the inner wall 62, in the region of the nasal bridge. This gap 68 enables the mask 10 to conform more closely to the user's face, at the region of the nasal bridge. This also reduces the possibility of irritation by rubbing of the relatively stiff inner wall 62 on the nose, thus providing a more comfortable mask. Although the inner wall 62 does help the sealing function by supporting the outer wall 64, it is not needed everywhere, and this region is selected to maximize comfort.

The side wall 60 of the cushion 40 terminates in an outer peripheral tongue 72 (FIGS. 5-7) of the cushion, for mounting to the shell 20. The tongue 72 is of a reduced material thickness as compared to the side wall 60. For example, the thickness of the tongue 72 may be from one quarter to one half the thickness of the side wall 60. The tongue 72 extends from the side wall 60 by a distance long enough for it to mount releasably in the gap 54 of the shell.

The tongue 72 terminates in a retaining flange 74. The retaining flange 74 extends for the entire extent of the tongue 72, in a direction transverse to the tongue. In the illustrated embodiment, the retaining flange 74 extends at substantially a right angle to the tongue 72. The retaining flange 74 may be of the same or substantially the same material thickness as the tongue 72.

The tongue 72 of the cushion 40 is inserted into the gap 54 between the retaining ring 50 and the shell side wall 24 to secure the cushion to the shell 20. The tongue 72 is inserted far enough into the gap 54 so that the flange 74 on the tongue engages in the notch 56 of the retaining ring 50. The flange 74 and the tongue 72 are captured between the retaining ring 50 and the side wall 24 of the shell 20. This engagement holds the cushion 40 on the shell 20. Because the retaining ring 50 and the gap 54 extend completely around the shell 20, and the tongue 72 extends completely around the cushion 40, the cushion is held securely on the shell around its entire extent.

The cushion 40 is removable from the shell for cleaning or replacement purposes. The user can pull with enough force to remove the tongue 72 and the retaining flange 74 from the gap 54 between the ring 50 and the shell side wall 24. In this manner, the cushion 40 is disengaged from the shell 20. After this is done, the same cushion 40 or another cushion 40 can be inserted and attached to the shell 20.

The headgear 80 of the mask 10 includes two side straps 82 (FIGS. 1-2 and 9-11). The side straps 82 are attached to opposite left and right sides of the mask shell 20 in identical manners. The attachment of one strap 82 will be described in detail.

The mask shell 20 includes a shell connector 84 (FIG. 11) for receiving the side strap 82. The shell connector 84 is in the form of a projection from the side wall 24 of the shell 20.

The shell connector 84 includes two side arms 85 that extend outward from the side wall 24 of the shell 20. The arms 85 are spaced apart from each other. A cross-arm 86 extends between the two arms 85, at a predetermined distance from the side wall 24. The cross arm 86 and the arms 85 are substantially co-planar and together define an opening 88 in the shell connector 84.

The shell connector 84 also includes a tab 90. The tab 90 is a portion of the shell connector 84 that extends from the cross arm 86, in a direction generally toward the side wall 24 of the shell 20. The tab 90 also extends out of the plane of the side arms 84, in a direction away from the user's face. The tab 90 has an end portion 92 that is spaced apart from the cross arm 86 by a predetermined distance.

The headgear 80 includes a strap connector 94 for engagement with the shell connector 84. The strap connector 94 includes a generally rectangular plastic loop 96 having four legs 98, 100, 102 and 104. The inner leg 98 of the loop 96 is secured on the end of the side strap 82 by folding over and connecting with a hook and loop fastener for adjustability.

The four legs 98-104 of the loop 96 define an opening 108 in the strap connector 94. The dimensions of the opening 108 are selected so that the shell connector 84 can fit inside and through the opening in the strap connector 94.

The strap connector 94 also includes a tab 110. The tab 110 of the strap connector 94 extends from the inner leg 98 of the strap connector loop 96, in a direction into the opening 108, for a predetermined distance. The tab 110 does not extend completely to the opposite (outer) leg 102 of the loop 96. Rather, the tab 110 has an end portion 112 that is spaced apart from the outer leg 102 of the loop 96, defining a gap 114. The tab 110 of the loop 96 is resiliently bendable relative to the legs 98-104 of the loop.

Figure 11:
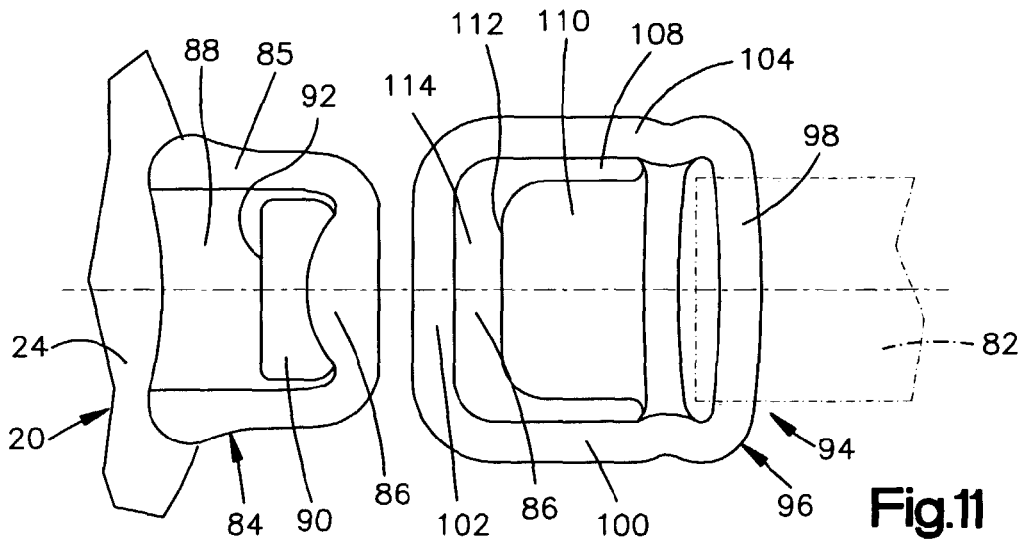
FIG. 11 is a view similar to FIG. 10 showing the strap connector in an unconnected condition.

The strap connector 94 is engageable with the shell connector 84 to connect the side strap 82 to the shell 20 in a releasable manner. The strap connector 94 is moved into a position adjacent to the shell connector 84 as shown in FIG. 11.

The tab 90 of the shell connector 84 is then inserted into the opening 108 in the strap connector 94, with the parts at a substantial angle to each other. The tab 90 of the shell connector 84 is, specifically, inserted into the gap 114 between the tab 110 and the outer leg 102 of the strap connector 94.

The outer leg 102 of the loop 96 engages the side arms 85 of the shell connector 84. The strap connector 94 is then pivoted downward relative to the shell connector 84, pivoting generally about the outer leg 102 of the loop 96.

The tab 110 of the strap connector 94 passes under the cross arm 86 of the shell connector 84. The cross arm 86 and the tab 90 of the shell connector 84 move through the gap 114 between the end portion 112 of the tab 110 on the strap connector 94, and the outer leg 102 of the loop 96.

The size of this gap 114, that is, the distance between the end portion 112 of the tab 10 on the strap connector 94, and the outer leg 102 of the loop 96, is slightly less than the combined length of the cross arm 86 and the tab 90 on the shell connector 84. Therefore, the tab 110 on the strap connector 94 must bend or flex by a small amount in order to enlarge this gap so that the tab on the shell connector 84 can pass through the gap.

The tab 110 on the strap connector 94 bends, then snaps back to its free position as it passes under the cross arm 86. This snapping movement is both audible and tactile, and indicates to the user that the side strap 82 is connected to the shell 20.

When the parts are thus connected, the end portion 112 of the tab 110 on the strap connector 94 is disposed in the opening 88 in the shell connector 84. At the same time, the outer leg 102 of the loop 96 on the strap connector 94 is on the opposite side of the arms 85 of the shell connector 84.

As a result, the shell connector 84 is captured in the loop 96 of the strap connector 94. This joining of the shell connector 84 with the strap connector 94 secures the side strap 82 to the mask shell 20.

This connection is loose enough so that when the side strap 82 is secured to the mask shell 20, the loop 96 of the strap connector 94 is pivotable relative to the shell connector 84. This freedom of movement enables the side straps 82 to be fitted more comfortably to the user's head.

To release the side straps 82, the user lifts the strap connector 94, pivoting it upward in a movement generally opposite the pivoting movement used to connect the two pieces. As this pivoting movement occurs, the tab 110 of the strap connector 94 deforms, bending or flexing a small amount as needed to enable it to pass under the cross arm 86 of the shell connector 84. As it passes, it snaps back to its starting or free position, with an audible and tactile snap. This snap indicates to the user that the side strap 82 is disconnected from the shell 20. The configuration of the shell connector 84 and the strap connector 94 permits the side strap 82 easily to be attached to and detached from the shell 20, with a minimal risk that the strap will be accidentally detached during use, for example, as the user moves around during sleep.

The forehead support assembly 30 (FIGS. 12-15) of the mask 10 is adjustable. The forehead support assembly 30 includes a support bar 120 and an adjuster 140.

The support bar 120 is a portion of the shell 20 that is fixed to the other parts of the shell including the shell side wall 24. The support bar 120 includes two spaced apart side walls 122 that define between them a slot 124. The side walls 122 have an arcuate configuration extending upward and inward from the side wall 24 of the shell 20. The side walls 122 have respective flanges 126 that extend inwardly toward each other. The center of curvature (or axis) 125 (FIG. 14) of the side walls 124 is spaced apart from the support bar 120 and other parts of the mask shell 20, rather than being located on the mask. The center of curvature in the illustrated embodiment would be within the user's head when the mask is in use.

The support bar 120 includes a flexible member 130 that extends upward from the shell side wall 24 into the slot 124 between the support bar side walls 122. The flexible arm 130 is formed as one piece with the shell 20 and the support bar 120. The flexible arm 130 has an outer end portion 132 that includes two pawls 134 on either side of a button 136. The button 136 is a portion of the support bar 120 that is manually engageable to effect flexing movement of the flexible arm 130 and thereby movement of the pawls 134 relative to the side walls 122 of the support bar 120. The pawls 134 are movable with the button 136 upon flexing of the flexible arm 130 in response to application of force to the button.

The adjuster 140 is a portion of the forehead support assembly 30 that is supported on the support bar 120 for movement relative to the support bar and the other parts of the shell 20. The adjuster 140 includes an arcuate engagement portion 142 that has the same center of curvature as the side walls 122 of the support bar 120. The engagement portion 142 has a laterally extending central wall 144 and two side walls 146 extending from the central wall. The lower portion of the central wall 144 includes an opening 148 for receiving the button 136.

Each one of the side walls 146 has a groove or slot 149 that receives a respective flange 126 of one of the side walls 122 of the support bar 120. This engagement, and only this engagement, supports the adjuster 140 on the support bar 120 for arcuate sliding movement about the center of curvature 125. Because the center of curvature 125 is spaced apart from the mask 10 including the shell 20 and the support bar 120, the adjuster moves in a wide arc. This provides more horizontal movement without much vertical movement, than would an adjuster pivoting about a pivot axis on the shell itself.

Each one of the side walls 146 of the engagement portion 142 of the adjuster 140 has a set of inwardly extending (toward the center of curvature) locking teeth 150. The locking teeth 150 extend from the side walls 146 and are disposed in the slot 124 of the support bar 120, between the side walls 122 of the support bar. The locking teeth 150 are presented toward and engageable by the pawls 134 of the support bar 120.

The adjuster 140 has an upper end portion 152 that extends upward from the engagement portion 142. The adjuster 140 has a strip-like or bar-like configuration and, as a result, the upper end portion 152 is not substantially wider than the engagement portion 142. Thus, the adjuster 140 when viewed from the front (as in FIG. 2) has an I-shaped configuration, rather than a T-shaped configuration.

The adjuster 140 (FIG. 13) has left and right slots 154 and 156 in its upper end portion 152. The slots 154 and 156 extend parallel to each other, through the material of the adjuster 140, from the front side surface to the back side surface.

The headgear 80 of the mask 10 includes a forehead strap assembly 160 (FIG. 2) that, in the embodiment shown in FIGS. 1 and 2, includes left and right forehead straps 162 and 164. The forehead straps 162 and 164 extend outward from a central location, above the shell 20, wrapping around the user's forehead, to help secure the mask 10 to the user's face. The two straps 162 and 164 are identical to each other. The straps 162 and 164 are made from a fairly thick, resilient material, so as to provide a cushioning effect when worn by a user. The two straps 162 and 164 may be joined to each other as one piece, on the side or back of the head.

Each one of the slots 154 and 156 in the upper end portion 152 of the adjuster 140 is dimensioned to accept one of the forehead straps 162 and 164. The left forehead strap 162 is passed through the left slot 154 (FIG. 2A) in the forehead adjuster 140. In a similar manner, the right forehead strap 164 is passed through the right slot 156 in the forehead adjuster 140. The left strap 162 is brought back on itself to form a loop 166. An end portion 161 of the left strap 162 is secured to another portion 163 of the left strap 162 with a suitable securing, such as a hook and loop fastener 165. Use of a hook and loop fastener 165, as illustrated, provides adjustability for the length of the left forehead strap 162. The right strap 164 is brought back on itself to form a loop. An end portion 161 of the right strap 164 is secured to another portion 168 of the right strap with a suitable securing, such as a hook and loop fastener 169. Use of a hook and loop fastener 169, as illustrated, provides adjustability for the length of the right forehead strap 164.

When the left and right straps 162 and 164 are connected with the forehead adjuster 140 in this manner, a relatively large amount of strap material is present between the forehead adjuster 140 and the user's forehead. This strap material, as mentioned above, is resilient. Therefore, a substantial cushion is present between the forehead support assembly 30 and the user's forehead. This cushion provides a very comfortable strap attachment, without the necessity for separate cushion members or cushioning pieces on the adjuster 140.

The engagement of the pawls 134 of the support bar 120, with the teeth 150 of the adjuster 140, (FIGS. 13-15) locks the adjuster in position relative to the support bar. To move the adjuster 140 relative to the support bar 120, the button 136, which is fixed to the support bar and thereby the shell 20, is depressed (pushed in, toward the forehead of the user). The flexible arm 130 bends. This bending movement causes the pawls 134 to move inward, out of engagement with the arcuate tooth sets 150 on the adjuster 140. The adjuster 140 is then free to move relative to the support bar 120. The user can move (slide) the adjuster 146 to any position within its range of motion, to accommodate varying head configurations including differing front to back distances between the nose and the forehead of the user. Releasing the button 136 allows the pawls 134 to move into engagement with the teeth 150, thereby locking the adjuster 140 in any selected one of its plurality of possible positions relative to the support bar 120 and the shell 20.

Because the button 136 is mounted on the shell 20, it can be pushed with one hand or finger that stays in place during the adjustment of the forehead support assembly 30. There is no need to simultaneously depress the button 136 and move it, which can be a more difficult operation, especially if the user can not directly see the parts, which is the case if the user is trying to adjust the mask 10 while wearing the mask.

Figure 16:
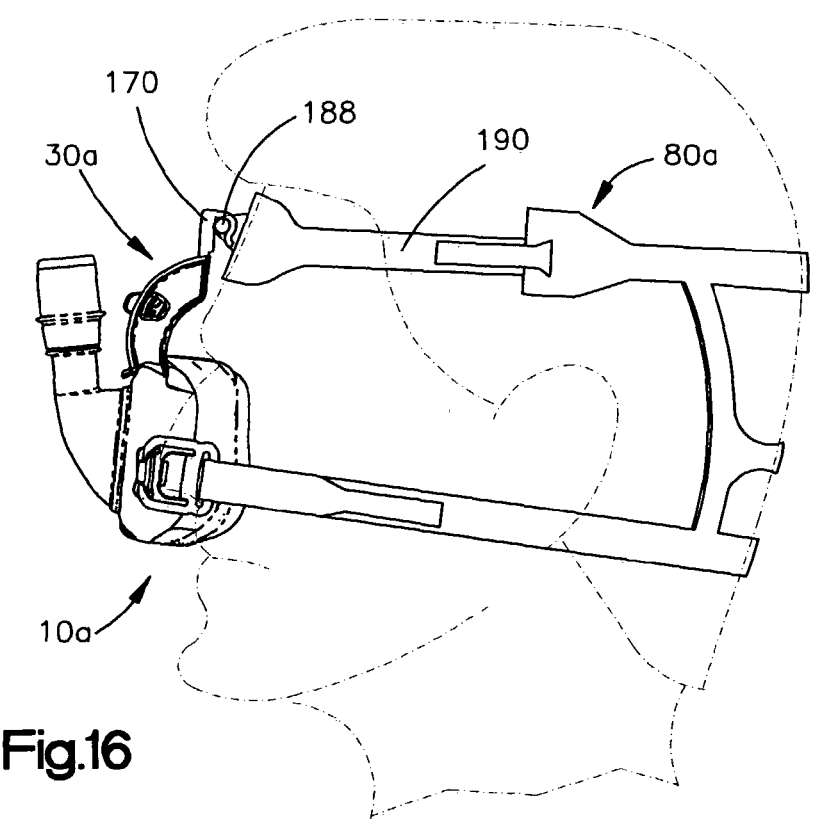
FIG. 16 is a side elevational view, similar to FIG. 1, of a mask including a forehead support in accordance with a second embodiment of the invention.
Figure 17:
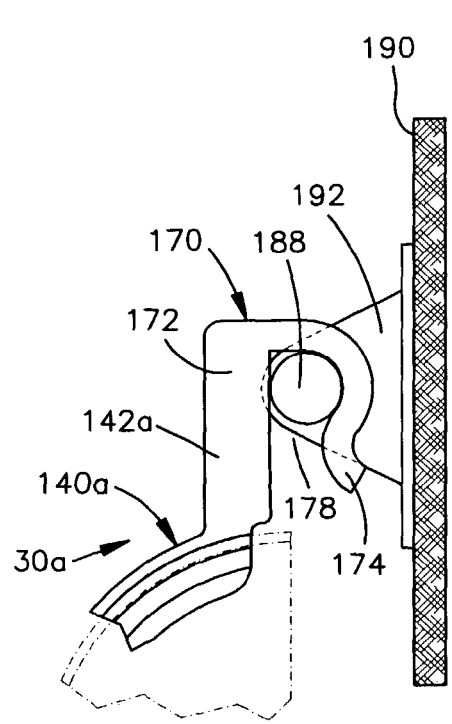
FIG. 17 is a schematic enlarged view of a portion of the forehead support of the mask of FIG. 16.
Figure 18:
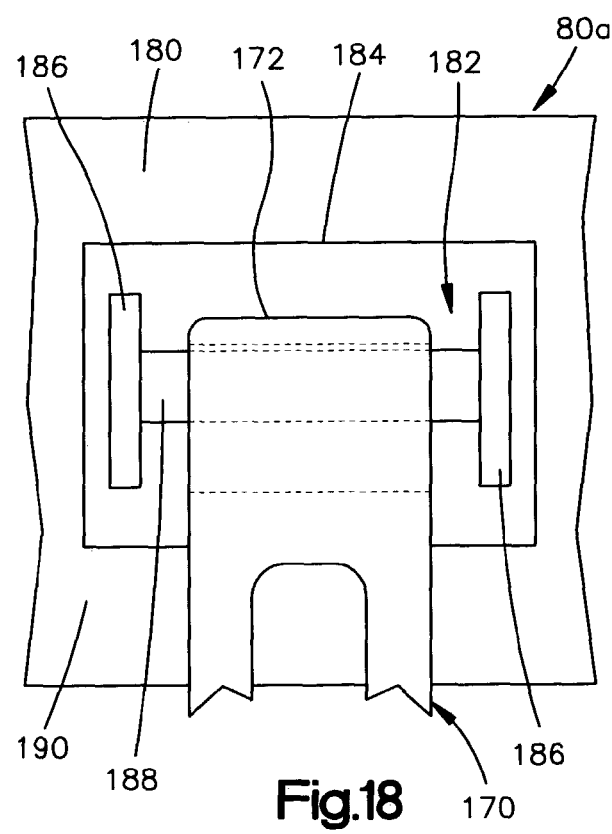
FIG. 18 is a schematic front elevational view of the forehead support portion shown in FIG. 17.

FIGS. 16-18 illustrate an alternative forehead support assembly 30a of a mask 10a. In the forehead support assembly 30a, the upper end portion 142a of the forehead adjuster 140a includes a snap hook 170.

The snap hook 170 has a multiply curved configuration including a body portion 172 and an end portion 174 that curves back toward the body portion. The end portion 174 is spaced apart from the body portion 172 by a predetermined distance to define a gap 178. The hook 170 is slightly resilient, so that the end portion 174 of the hook is resiliently movable away from the body portion 172.

Associated with the forehead support assembly 30a is a forehead strap assembly 80a that includes a forehead strap 190 and a stiffener or other type of reinforcing member 180. A clevis 182 is fixed to the reinforcing member 180. The clevis 182 has a base 184 and two ends 186, spaced apart in a forked configuration. A cylindrical pin 188 extends between the ends 186 of the clevis 182, in a direction parallel to the length of the forehead strap 190. The pin 188 and the base 184 of the clevis 182 define a passage 192. The thickness (diameter) of the pin 188 is slightly greater than the width of the gap 178 in the snap hook 170.

To attach the shell 20 to the forehead strap 190, the user places the snap hook 170 adjacent the pin 188. The end portion 174 of the hook 170 is moved through the passage 192 in the clevis 182; the pin 188 moves through the gap 178 in the hook. As this movement occurs, the snap hook 170 resiliently deforms, with its end portion 174 bending slightly outward, to fit over the pin 188. After the pin 188 passes through the gap 178 in the hook 170, the hook resiliently returns to its free state.

The snap fit engagement of the hook 170 with the pin 188 secures the forehead support assembly 30a to the forehead strap 190. This helps to hold the mask 10 in place on the user's face. In addition, the clevis and pin combination supports the hook 170 on the pin 188 for pivotal movement relative to the forehead strap 190. As a result, the forehead support assembly 30a and the forehead strap 80a are adjustable relative to each other by pivoting. This pivoting movement can accommodate wearers' foreheads of differing slopes or sizes.

Figure 19:
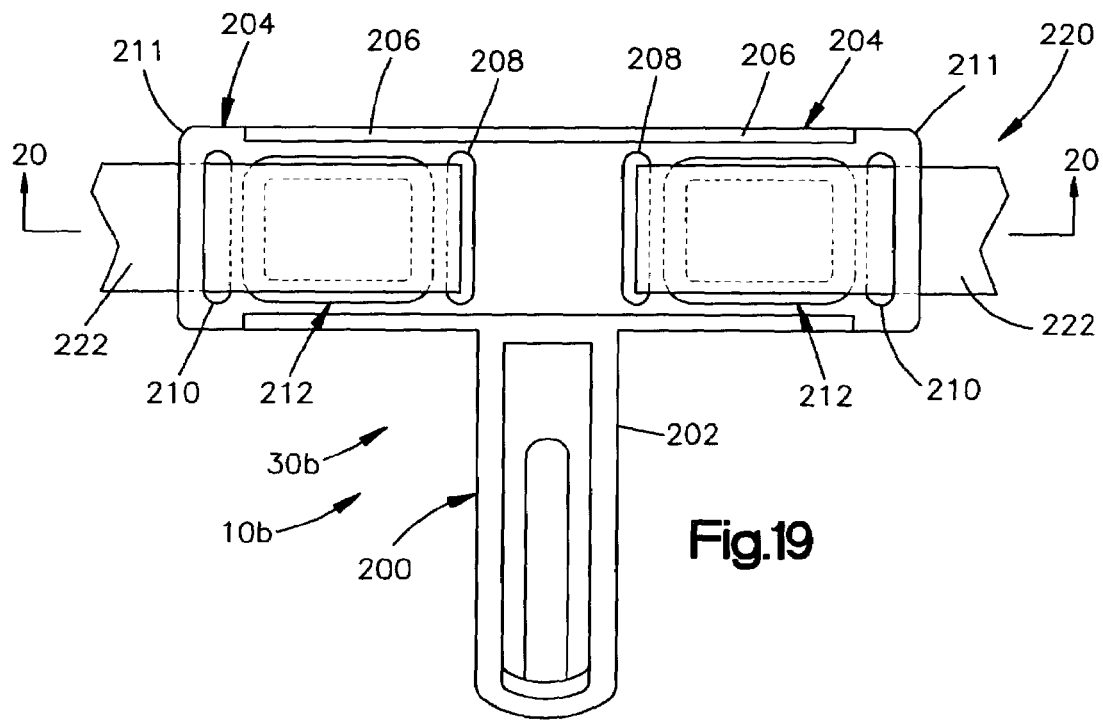
FIG. 19 is a front elevational view of a portion of an adjuster portion of a forehead support assembly in accordance with a further embodiment of the invention.
Figure 20:
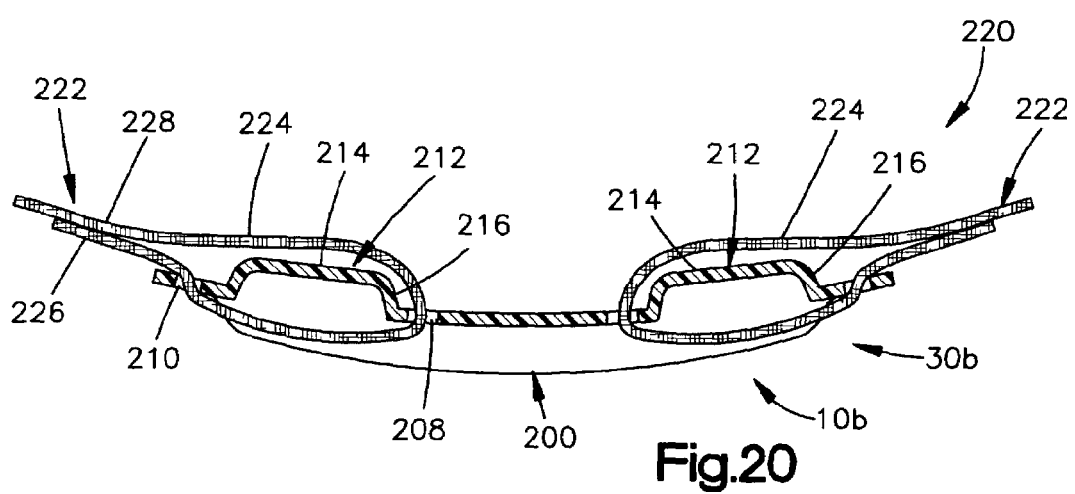
FIG. 20 is a sectional view of the adjuster taken along line 20-20 of FIG. 19.

FIGS. 19-20 illustrate a second alternative forehead support assembly 30b for a mask 10b. The forehead support assembly 30b includes a movable member or adjuster 200 having a T-shaped configuration when viewed from the front, as for example in FIG. 19.

The T-shaped configuration of the movable member 200 includes a base 202 and two arms 204 that extend laterally from the base. The arms 204 are mirror images of each other. Each arm 204 has a main body portion 206 that has a non-planar configuration (as can be seen in FIG. 20) adapted to a typical forehead curvature.

The main body portion 206 of each arm 204 has an inner slot 208 and an outer slot 210. The inner slot 208 is located closer to the base 202 of the adjuster 200, and the outer slot 210 is located farther from the base, near the outer end portion 211 of the arm 204. The slots 208 and 210 extend vertically in the arms 204.

The movable member 200 is made from a relatively hard material so that it can bear the load of the forehead straps. This relatively hard material can be uncomfortable to the user if the movable member 200 rides against the user's forehead.

Located between the slots 208 and 210, on each arm 204, is a spacer 212. The spacer 212 is a portion of the arm 204 that projects, or protrudes, in a direction toward the forehead of the user, from the main body portion 206 of the arm. Thus, the spacer 212 projects toward the center of curvature of the arms 204. The purpose of the spacer 212 is to keep the forehead adjuster 200, and specifically the main body portion 206 of the arm 204, spaced apart from the user's forehead, to prevent rubbing, irritation, etc.

In the embodiment illustrated in FIGS. 19 and 20, the spacer 212 is molded as one piece with the main body portion 206, as a rectangular box-shaped projection. The spacer 212 has an outer end wall 214 that is spaced apart from the plane of the main body portion 206: The outer end wall 214 is connected with the main body portion of the arm by four side walls 216, to form the box-shaped configuration. The outer end wall 214 of the spacer 212 is the portion of the arm 204 that is closest to the forehead of the user, closer than the end portion 211 of the arm, even taking into account the overall curved configuration of the arm.

The headgear of the mask includes a forehead strap assembly 220 that includes two forehead straps 222. The forehead straps 222 extend outward from a central location, wrapping around the forehead, to help secure the mask to the user's face. The two straps 222 are identical to each other. The straps 222 are made from a fairly thick, resilient material, so as to provide a cushioning effect when worn by a user.

Each strap 222 is passed through the inner and outer slots 208 and 210 and is brought back on itself to form a loop 224. The looped strap 222 extends around the spacer 212, overlying the outer end wall 214 of the spacer. The loop 224 is disposed between the spacer 212 and the forehead of the user. The combination of the spacer 212 and the loop 224 maintains the member 200 in a position spaced apart from (not in contact with) the forehead of the user, even taking into account the overall curved configuration of the arms 204.

In other embodiments, the spacers 212 need not be formed as one piece with the arms 204. For example, the spacers 212 could be separate elements that are connected with the arms 204 to provide the spacing function. The spacers 212 could also be adjustable in thickness, either within themselves, or by providing separate spacers of differing thicknesses.

Figure 21:
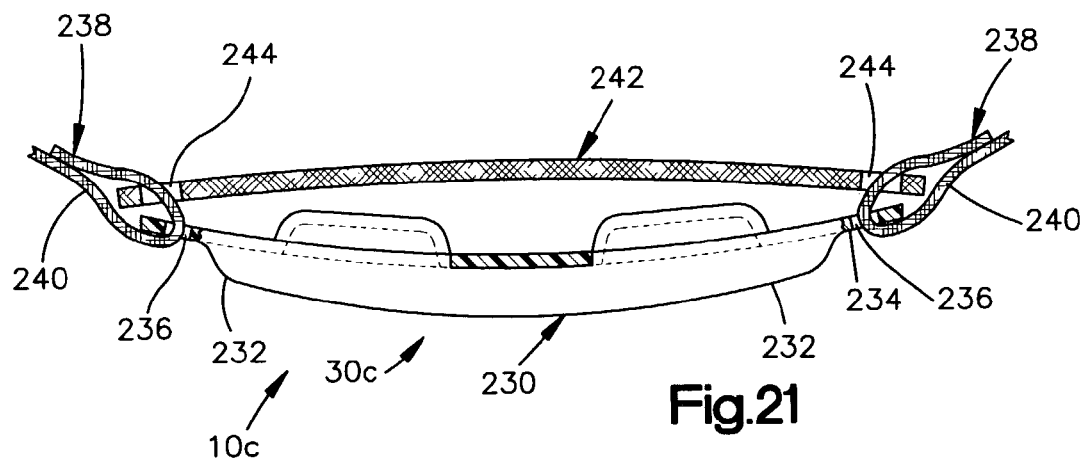
FIG. 21 is a view similar to FIG. 20 of a further forehead adjuster and forehead support assembly.

FIG. 21 illustrates a third alternative forehead support assembly 30c of a mask 10c. In the forehead support assembly, the movable member 230 has a T-shaped configuration when viewed from the front, similar to FIG. 19. The T-shaped configuration includes a base and two arms 232 each having an outer end portion 234 with a vertically extending slot 236 that is dimensioned to accept one of the forehead straps 238.

The left forehead strap 238 is passed through the slot 236 in the left arm 232 and is brought back on itself to form a loop 240. In a similar manner, the right forehead strap 238 is secured to the right arm 232 to form a loop 240 in the right strap.

A separate cushioning strap 242 extends between the left and right forehead straps 238. The cushioning strap 242 may be made from the same material as the left and right forehead straps 238. The cushioning strap 242 has first and second slots 244 located at opposite ends of the cushioning strap. The loops 240 of the forehead straps 238 extend through the slots 244. As a result, the cushioning strap 242 is located inward of the forehead adjuster 230, between the forehead adjuster and the user's forehead.

The cushioning strap 242 is slightly longer than the distance between the two slots 236 at the outer ends 234 of the arms 232 of the forehead piece 230. The length of the cushioning strap 242 is selected so that when the mask 10c is in place, the cushioning strap self-adjusts to a position snug against the user's forehead and also snug against the arms 232 of the forehead piece 230. Thus, the cushioning strap 242 provides a cushioning effect for the forehead piece 230, increasing the comfort level of the wearer of the mask 10c.

Figures 22, 23:
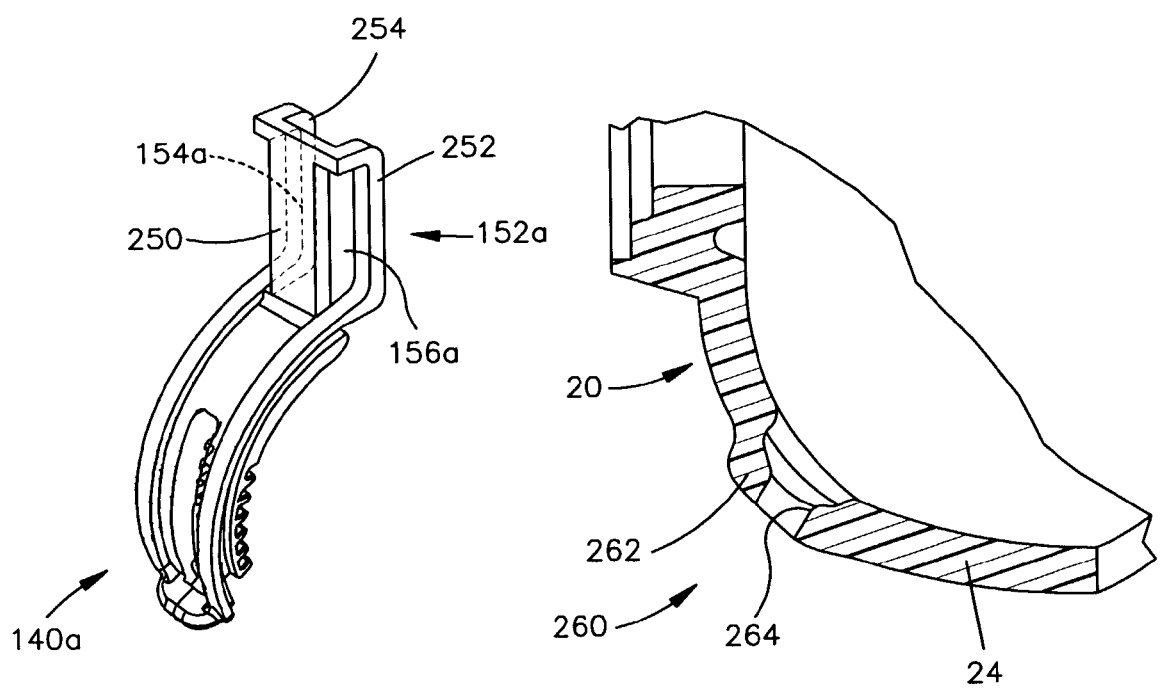
FIG. 22 is a view similar to FIG. 14 of another forehead adjuster.
FIG. 23 is a sectional view of an exhalation opening portion of the mask of FIG. 1.

FIG. 22 illustrates a forehead adjuster 140a that is constructed in accordance with a further embodiment of the invention. The adjuster 140a is similar to the adjuster 140 (FIG. 13) and is adjustable in the same manner. The upper end portion 152a of the adjuster 140a, rather than having a planar, bar-shaped configuration like the upper end portion of the adjuster 140, has a three-dimensional, cut-out configuration.

The upper end portion 152a of the adjuster 140a (FIG. 22) includes three generally vertically extending posts 250, 252 and 254 that are spaced apart from each other. The central post 250 is an extension of the central wall 144a of the adjuster 140a in a vertical direction rather than continuing the arcuate shape of the central wall. The side posts 252 and 254 are vertical extensions of the side walls 146a of the adjuster 140a. The side posts 252 and 254 curve up and forward to meet the central post 250.

A pair of slots are formed in the upper end portion 152a of the adjuster 140a. A right slot 156a is defined between the right side post 252 and the central post 250. A left slot 154a is defined between the left side post 254 and the central post 250.

A forehead strap assembly (not shown) can be connected with the adjuster 140a. A right strap would pass through the right slot 156a, wrapping around the right side post 252. A left strap would pass through the left slot 154a, wrapping around the left side post 254. Alternatively, a single strap could pass through both slots 154a and 156a, in front of the left and right side posts 252 and 254 and behind the central post 250.

FIGS. 4 and 23 illustrate an exhalation vent portion 260 of the mask 10. The vent portion 260 includes a thickened wall area 262 in the lower part of the side wall 24 of the shell 20. Five circular exhalation openings 264 are formed at equally spaced intervals in the thickened area 262. The exhalation openings 264 extend from the exterior of the mask 10 to the central chamber 32 of the shell 20. The exhalation openings 264 enable exhaled air to flow out of the mask 10.

The exhalation openings 264 are located below (when the mask is in use) the gas inlet aperture 34. This location is selected to enable efficient venting of the mask 10, as it is substantially in line with the nasal passages. It is also an area chosen to minimize annoyance from the exhaled air, either to the user or to a bed partner.

The exhalation openings 264 are configured to vent air at a thirty-five degree angle from vertical (thirty five degrees up from straight down, if the user is standing). This angle is 55 degrees from the axis of the gas inlet. This angle is selected to minimize irritation from exhaled air hitting the user's chest, while also minimizing irritation to someone close by, for example a bed partner.

The circular openings 264 provide less noise than a slot. The total flow area of the five openings 264 is selected to optimize venting and pressures in the mask while minimizing noise.

From the above description of the invention, those skilled in the art will perceive improvements, changes, and modifications in the invention. For example, the present invention is shown as being incorporated in a nasal mask only. The invention may be incorporated into a combined nasal/mouth mask (a mask with a central cavity 16 and face cushion 14 large enough to encompass the user's nose and mouth), or in a mouth mask only. Such improvements, changes, and modifications within the skill of the art are intended to be included within the scope of the appended claims.

Having described the invention, we claim:

1. A mask including: a shell; a cushion connected with said shell; said shell having a side wall; a retaining ring permanently secured to the shell inside said side wall, said side wall and said retaining ring defining a gap between said side wall and said retaining ring, said gap extending around said shell, wherein said retaining ring has a notch in cross-section; wherein said shell includes a plurality of projecting posts, and said retaining ring includes a plurality of sleeves receiving said posts to permanently secure said retaining ring inside said side wall of said shell; said cushion having a side wall with an outer peripheral edge portion including a tongue extending around said cushion, said tongue having a retaining flange that extends transverse to the tongue in cross-section; said retaining flange of said cushion tongue and said notch of said retaining ring being configured such that said tongue is repeatably insertable into said gap while the retaining ring is secured to the shell so that the retaining flange of the tongue engages the notch of the retaining ring to secure said cushion to said shell and the retaining flange of the tongue is repeatably removeable from the notch of the retaining ring while the retaining ring is secured to the shell to remove the cushion from the shell.

2. The mask of claim 1 wherein said sleeves are heat staked on said posts to permanently secure the retaining ring to the shell.

3. A nasal mask including:
a shell; and
a cushion connected with said shell for engagement with the face of a user;
said cushion having a side wall, an inner wall extending from the side wall transverse to said side wall, and an outer wall extending from the side wall transverse to said side wall;
wherein said outer wall is defined by first and second sides that are spaced apart by a thickness of the outer wall, wherein said first side of the outer wall is adapted to engage and seal against a face of a user of the mask;
wherein both of said first and second sides of said outer wall of said cushion extend from said side wall extending completely around said cushion;
wherein said inner wall is defined by first and second sides that are spaced apart by a thickness of the inner wall, wherein said first side of said inner wall is spaced apart from said second side of said outer wall;
wherein both of said first and second sides of said inner wall of said cushion are discontinuous in a nasal bridge region of said cushion, such that a gap is formed between ends of the inner wall in said nasal bridge region.

4. A nasal mask as set forth in claim 3 wherein said inner wall of said cushion is thicker and stronger than said outer wall of said cushion for supporting said outer wall.

5. A nasal mask as set forth in claim 3 wherein the outer wall extends laterally inward from the side wall, and the inner wall extends around the side wall.

6. A nasal mask as set forth in claim 3 wherein the inner wall of the cushion is stiffer than the outer wall for supporting the outer wall.

7. A nasal mask as set forth in claim 6 wherein the inner wall of the cushion is thicker than the outer wall and is spaced from the user's face when the outer wall seals against a face of a user of the mask.

8. A nasal mask as set forth in claim 3 wherein the inner wall of the cushion is thicker than the outer wall and is spaced from the user's face when the outer wall seals against a face of a user of the mask.

9. The mask of claim 3 wherein said inner wall of said cushion does not extends from the side wall in said nasal bridge region of said cushion.

10. The mask of claim 3 wherein a gap is formed between two ends of the inner wall of said cushion in said nasal bridge region of said cushion.

11. A mask including:
a shell having a side wall;
a cushion;
a retaining ring permanently secured to the shell inside said side wall by sleeves that are heat staked on posts;
said side wall and said retaining ring defining a gap between said side wall and said retaining ring, said gap extending around said shell wherein said retaining ring has a notch in cross-section;
said cushion having a side wall with an outer peripheral edge portion including a tongue extending around said cushion, said tongue having a retaining flange that extends transverse to the tongue in cross-section;
said retaining flange of said cushion tongue and said notch of said retaining ring being configured such that the tongue is repeatably insertable into said gap while the retaining ring is secured to the shell so that the retaining flange of the tongue engages the notch of the retaining ring to secure said cushion to said shell and the retaining flange of the tongue is repeatably removeable from the notch of the retaining ring while the retaining ring is secured to the shell to remove the cushion from the shell.

12. A method of assembling, cleaning, and reassembling a mask comprising: securing a retaining ring to a shell inside a side wall of the shell to define a gap and a notch between said side wall and said retaining ring that extends around the shell; inserting a tongue of the cushion into said gap while the retaining ring is secured to the shell so that a retaining flange that extends transverse to the tongue engages the notch to secure said cushion to said shell; a retaining ring permanently secured to the shell inside said side wall by sleeves that are heat staked on posts: removing the tongue and retaining flange from the gap and notch while the retaining ring is secured to the shell to remove the cushion from the shell; cleaning said cushion; inserting the tongue of the cushion into said gap while the retaining ring is secured to the shell so that the retaining flange of the tongue engages the notch to resecure said cushion to said shell.

13. A mask as set forth in claim 12 wherein said securing said retaining ring to said shell comprises heat staking a plurality of sleeves of said retaining ring onto a plurality of projecting posts of said shell.

\* \* \* \* \*

UNITED STATES PATENT AND TRADEMARK OFFICE
CERTIFICATE OF CORRECTION

PATENT NO. : 7,621,274 B2
APPLICATION NO. : 10/601729
DATED : November 24, 2009
INVENTOR(S) : Sprinkle et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1683 days.

Signed and Sealed this

Twenty-sixth Day of October, 2010

David J. Kappos
*Director of the United States Patent and Trademark Office*